United States Patent [19]

Abend

[11] 4,311,692
[45] Jan. 19, 1982

[54] TERTIARY AMINE PERSONAL CARE COMPOSITION

[75] Inventor: Phillip G. Abend, Los Angeles, Calif.

[73] Assignee: Quad Chemical Corporation, Long Beach, Calif.

[21] Appl. No.: 181,216

[22] Filed: Aug. 25, 1980

Related U.S. Application Data

[62] Division of Ser. No. 101,775, Dec. 10, 1979, Pat. No. 4,281,201.

[51] Int. Cl.$^3$ .......................... A61K 7/06; A61K 7/08; A61K 7/09; A61K 47/00
[52] U.S. Cl. ...................................... 424/70; 424/170; 424/365
[58] Field of Search .......................... 424/170, 365, 70

[56] References Cited

U.S. PATENT DOCUMENTS

| | | | |
|---|---|---|---|
| 2,856,363 | 10/1958 | Brennan | 252/33.6 |
| 3,239,565 | 3/1966 | Kreevoy et al. | 564/503 |
| 3,365,435 | 1/1968 | Adams et al. | 525/6 |
| 3,457,313 | 7/1969 | Baker | 564/473 |
| 3,558,711 | 1/1971 | Eckert et al. | 564/507 |
| 3,697,423 | 10/1972 | Sundby et al. | 252/8.8 |
| 3,928,422 | 12/1975 | Sundby | 560/151 |

*Primary Examiner*—Alan L. Rotman
*Attorney, Agent, or Firm*—Richard H. Zaitlen

[57] ABSTRACT

This invention relates to compounds of the formula:

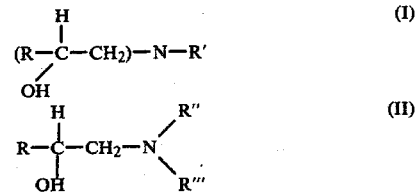

including derivatives thereof. The subject compounds have been found to be particularly useful as cationic emulsifiers and exhibit many desirable properties in connection with personal care compositions.

9 Claims, No Drawings

TERTIARY AMINE PERSONAL CARE COMPOSITION

This is a division of application Ser. No. 101,775, filed Dec. 10, 1979, now U.S. Pat. No. 4,281,201, issued July 28, 1981.

BACKGROUND OF THE INVENTION

1. Field of the Invention

The present invention relates to the field of novel amine compounds, and more specifically, to novel tertiary amine compounds and their use in water-base personal care compositions.

2. Prior Art

The use of cationic emulsifiers in a wide range of compositions is well recognized in the prior art. Such compositions include, for example, hair conditioners, cream rinses, lotions, and the like. In addition, cationic emulsifiers have also been used in other compositions such as pesticides, antistatic agents, etc. With respect to the health care industry, some cationic emulsifiers have proved to be especially useful inasmuch as they have been found to be less irritating than some anionic emulsifiers. The problem with skin irritation, however, still persists irrespective of whether a cationic or anionic emulsifier is used. As a result, the amount of emulsifier used in connection with any personal product is subject to a great degree of scrutiny.

Specific compounds useful as cationic emulsifiers are disclosed in U.S. Pat. No. 3,954,873. These compounds are the reaction products of branched chain olefin oxides with amines to yield branched chain alkyl amino alcohols. One of the shortcomings associated with the compounds disclosed in this patent is that they are believed to be liquids at room temperature. A liquid can be very difficult to handle and measure in many situations. As a result, it is difficult to determine exactly how much of such compound is being added. This is especially important if such compounds are being used in compositions which are to be applied to the skin or hair. Accordingly, care must be used to ensure that only the right amount of emulsifier is added in order to prevent possible irritation to the skin or other area of the body.

Reference is also made to an article published in *Zhurnal Obshchei Khimii* Volume 10, pages 2367–2368 October, 1974, entitled "Cationic Surface-Active Substances Derived from D-Sorbitol." This article teaches the use of various amines as cationic compounds. Yet other similar compounds are disclosed in the *Journal of the American Oil Chemists Society*, Volume 56(4)537(1979).

A review of all prior art references set forth above indicates that none of them teach or render obvious applicant's specific compounds which exhibit a number of desirable properties. Thus, the present invention represents an advancement in the art of organic amine compounds, and more specifically, in the area of cationic tertiary amine emulsifiers and their use in personal care products.

BRIEF SUMMARY OF THE INVENTION

The present invention relates to tertiary amines, acid salts and the salts thereof such as, for example, the hydrocloric lactic salts, citric acid salts and the phosphoric acid salts. These tertiary amines are generally represented by the Formula I or II

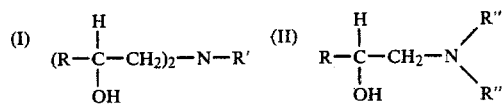

wherein R is a linear $C_8$ to $C_{20}$ alkyl group and R' is a hydroxyalkyl or polyhydroxyalkyl group containing from 1 to 10 carbon atoms, and having from one to five hydroxyl groups per R', and, individually, R" and R''' are alkyl, hydroxyalkyl or polyhydroxyalkyl groups, each containing one to six carbon atoms and from one to five hydroxyl groups per R" or R'''. Preferably R" and R''' are each selected from the group consisting of:

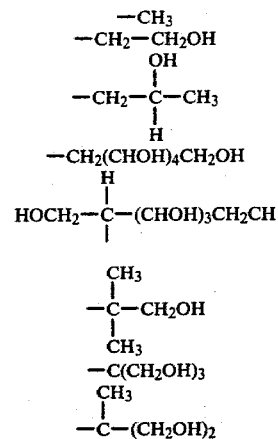

Preferably R', R" and R''' are methyl, ethyl, hydroxyethyl, hydroxypropyl, hydroxybutyl, or pentahydroxyhexyl radicals.

The tertiary amines set forth in Formula I or II are the result of reacting linear α-olefin oxides of the Formula III:

wherein R is an alkyl group having from 8 to 20 carbon atoms, with an amino alcohol containing one to five hydroxyl groups per primary or secondary amine group. Such amino alcohols include, for example, monoethanolamine, monoisopropanolamine, N-methylethanolamine, diethanolamine, diisopropanolamine, N-methylglucamine, aminoethylpropanediol, and tris(hydroxmethyl) aminomethane.

When the reaction of the linear α-olefin oxide with the primary amine is in a 2:1 molar ratio, the tertiary amine produced is represented by the general Formula I. When the reaction of the linear α-olefin with the secondary amines is a 1:1 molar ratio, the tertiary amine is represented by the Formula II.

The amines of the present invention (as well as their salts) have been found to be particularly useful in connection with personal care preparations. The amines of the present invention are cationic in nature and are generally waxy solids. The cationic nature of the compounds of the present invention renders them substantive to the negative centers of the hair and skin. In addition, some of the compounds of the present invention are solids which means that they can be accurately weighed and measured, but yet readily dispersed in a wide range of liquids including water, alcohol, etc.

Thus, problems associated with difficult-to-measure liquids are substantially overcome.

The novel features of the present invention together with the further objectives and advantages thereof, will be better understood from the following description considered in connection with the examples in which presently preferred enbodiments of the invention are illustrated. It is to be expressly understood, however, that the examples are for the purpose of illustration and description only, and are not intended as a definition of the limits of the invention.

DETAILS OF DESCRIPTION OF THE INVENTION

As stated above, the present invention is directed to a novel class or tertiary amines represented by Formula I or II. These amines are prepared by reacting an α-olefin of the Formula III $$R-\underset{H}{\overset{|}{C}}\underset{\diagdown O \diagup}{-}CH_2 \qquad (III)$$

with amines of Formula IV or V $$(IV) \quad H_2N-R' \qquad (V) \quad HN\underset{\diagdown R'''}{\diagup R''}$$

wherein R, R', R", and R''' are as defined in the Summary of the Invention above.

Examples of the amines of Formula IV include, monoethanolamine, monoisopropanolamine, aminomethylpropanol, aminoethylpropanediol, tris(hydroxymethyl) aminomethane. Examples of amines of Formula V include, N-methylethanolamine, diethanolamine, diisopropanolamine. N-methylglucamine.

It has been discovered that by using only linear -olefin oxides to make the compounds described in Formula III, one can obtain tertiary amines which are solids at room temperature when R is $C_{12}$ to $C_{16}$. The solid compounds are much easier to handle and measure than the liquids of the prior art. This, as stated above, is one advantage over the prior art.

The compounds of the present invention also have advantageous emulsification and cationic properties. This had led to their use in personal care compositions as well as other uses where emulsifiers are desirable. While not to be bound by any theory, it is believed that since the alkyl group is linear rather than branched, the cationic center is more readily shifted to the end of the alkyl chain and thus is more easily accessible for reaction.

The novel tertiary amines of the present invention are produced by reacting epoxides of Formula III with the amines of Formula IV or V. Generally, this reaction can be conducted at temperatures within the range of about 60° C. to 200° C., and more preferably, from about 100° C. to 170° C. If desired, an inert or nonoxidizing atmosphere can be maintained such as by employing nitrogen in the reaction vessel. Solvents seen as water, isopropanol, butyl alcohol, etc. can also be used if desired.

When it is desirable to form the salt of the amines of the present invention, the tertiary amine is further reacted stoichiometrically with an acid such as hydrochloric acid, lactic acid, citric acid or phosphoric acid to yield the corresponding salt.

Illustrative of the foregoing discussion and description, but again, not to be interpreted as any limitation on the scope of the present invention, reference is made to the following examples.

EXAMPLE 1

A 500 ml four neck round bottom flask equipped with a stirrer, thermometer, reflux condenser, and nitrogen inlet tube was charged with 98.3 gm of 1,2-epoxydodecane, 0.5 mole based on an oxirane oxygen content of 8.55% and 98.2 gm of N-Methyl glucamine, 0.5 moles. With mild nitrogen purging, the mixture was stirred and heated to 110° C. A rapid exotherm set in, causing the temperature to rise to 178° C. Stirring was continued without external heating until the temperature fell to 110° C. The molten mass was cast into an aluminum pan. The product had the following analytical values:

| Base Value | 147.88 mg |
|---|---|
| Hydroxyl Value | 861.14 mg |
| Primary Amine | 0 meq./gm. |
| Secondary Amine | 0.25 meq./gm. |
| Tertiary Amine | 2.59 meq./gm. |

These data show the product obtained to be the compound of the formula:

$$C_{10}H_{21}CHOHCH_2\underset{\underset{CH_3}{|}}{N}CH_2(CHOH)_4CH_2OH$$

Upon solidification, this product, a light tan solid, exhibited a melting point range of 95–100° C.

EXAMPLE 2

A one liter four neck round bottom flask equipped with a stirrer, thermometer, reflux condenser, and nitrogen inlet tube was charged with 228 g of 1,2-epoxyoctadecane, 0.78 mole based on an oxirane oxygen content of 5.48% and 152 g of N-methyl glucamine. 0.78 mole. With mild nitrogen purging, the mixture was stirred and heated to 130° C. A rapid exotherm set in, causing the temperature to rise to 185° C. Stirring was continued without external heating until the temperature fell to 130° C. The molten mass was cast into an aluminum pan. The product had the following analytical values:

| Base Value | 113.0 mg |
|---|---|
| Hydroxyl Value | 714.7 mg |
| Primary Amine | 0.0 meq./gm. |
| Secondary Amine | 0.04 meq./gm. |
| Tertiary Amine | 2.00 meq./gm. |

These data show the product obtained to be the compound of the formula:

$$C_{16}H_{33}CHOHCH_2\underset{\underset{CH_3}{|}}{N}CH_2(CHOH)_4CH_2OH$$

Upon solidification, this product, a light, tan, hard wax exhibited a melting point range of 93–98° C.

EXAMPLE 3

A one liter four neck round bottom flask equipped with a stirrer, thermometer, reflux condenser, and nitrogen inlet tube was charged with 288 g of 1,2-epoxyoctadecane, 1.0 mole based on an oxirane oxygen content of 5.55% and 105 g of diethanolamine 1.0 mole. With mild nitrogen purging, the mixture was stirred and heated to 135 degrees C. A rapid exotherm set in, causing the temperature to rise to 190° C. Stirring was continued without external heating until the temperature fell to 120° C. The molten mass was cast into an aluminum pan. The product had the following analytical values:

| Base Value | 143.75 mg |
| --- | --- |
| Hydroxyl Value | 427.07 mg |
| Primary Amine | 0.0 meq./gm. |
| Secondary Amine | 0.14 meq./gm. |
| Tertiary Amine | 2.41 meq./gm. |

These data show the product obtained to be the compound of the formula:
$C_{16}H_{33}CHOHCH_2N(CH_2CH_2OH)_2$ Upon solidification, this product, an off-white wax, exhibited a melting point range of 44–48° C.

EXAMPLE 4

A 500 ml four neck round bottom flask equipped with a stirrer, thermometer, reflux condenser, and nitrogen inlet tube was charged with 173 gm of 1,2-epoxydecane, 1.0 mole based on an oxirane oxygen content of 9.22% and 75 gm of N-methylethanolamine, 1.0 mole. With mild nitrogen purging, the mixture was stirred and heated to 100° C. A rapid exotherm set in, causing the temperature to rise to 170° C. The mixture was maintained at 170° C. for 1 hour and then stirring was continued until the mixture cooled to room temperature. The resulting fluid was dark amber in color. The product had the following analytical values:

| Base Value | 203.57 mg |
| --- | --- |
| Hydroxyl Value | 445.14 mg |
| Primary Amine | 0 meq./gm. |
| Secondary Amine | 0.01 meq./gm. |
| Tertiary Amine | 3.63 meq./gm. |

These data show the product obtained to be the compound of the formula:

$$C_8H_{17}CHOHCH_2N(CH_3)-CH_2CH_2OH$$

EXAMPLE 5

A one liter four neck round bottom flask equipped with a stirrer, thermometer, reflux condenser, and nitrogen inlet tube was charged with 346 gm of 1,2-epoxydecane, 2.0 mole based on an oxirane oxygen content of 9.22% and 61 gm of monoethanolamine, 1.0 mole. With mild nitrogen purging, the mixture was stirred and heated to 100° C. A rapid exotherm set, causing the temperature to rise to 235° C. Stirring was continued without external heating until the temperature fell to 130° C. The resulting fluid was light amber in color. The product had the following analytical values:

| Base Value | 135.05 mg |
| --- | --- |
| Hydroxyl Value | 391.95 mg |
| Primary Amine | 0.04 meq./gm. |
| Secondary Amine | 0 meq./gm. |
| Tertiary Amine | 2.38 meq./gm. |

These data show the product obtained to be the compound of the formula:

$(C_8H_{17}CHOHCH_2)_2N-CH_2CH_2OH$

EXAMPLE 6

A three liter four neck round bottom flask equipped with a stirrer, thermometer, reflux condenser, and nitrogen inlet tube was charged with 946 g of 1,2-epoxyoctadecane, 3.24 moles based on an oxirane oxygen content of 5.48% and 431 g of diisopropanolamine, 3.24 moles. With mild nitrogen purging, the mixture was stirred and heated to 100° C. A slow exotherm set in, causing the temperature to rise to 150° C. After the temperature fell to 130° C. the temperature was raised to 150° C. again with a very mild exotherm to 160° C. Stirring was continued without external heating until the temperature fell to 100° C. The molten mass was cast into an aluminum pan. The product had the following analytical values:

| Base Value | 132.69 mg |
| --- | --- |
| Hydroxyl Value | 379.29 mg |
| Primary Amine | 0.02 meq./gm. |
| Secondary Amine | 0.00 meq./gm. |
| Tertiary Amine | 2.35 meq./gm. |

These data show the product obtained to be the compound of the formula:

$C_{16}H_{33}CHOHCH_2N(CH_2CHOHCH_3)_2$

Upon solidification, this product, an off-white soft wax, exhibited a melting point range of 29–31 degrees C.

EXAMPLE 7

A two liter four neck round bottom flask equipped with a stirrer, thermometer, reflux condenser, and nitrogen inlet tube was charged with 1232 g of 1,2-epoxyoctadecane 4.28 moles based on an oxirane oxygen content of 5.55% and 130 g of monothanolamine, 2.14 moles. With mild nitrogen purging, the mixture was stirred and heated to 100° C. A rapid exotherm set in, causing the temperature to rise to 180° C. Stirring was continued without external heating until the temperature fell to 70° C. The molten mass was cast into an aluminum pan. The product had the following analytical values:

| Base Value | 85.03 mg |
| --- | --- |
| Hydroxyl Value | 249.57 mg |
| Primary Amine | 0.02 meq./gm. |
| Secondary Amine | 0.09 meq./gm. |
| Tertiary Amine | 1.41 meq./gm. |

These data show the product obtained to be the compound of the formula:

$(C_{16}H_{33}CHOHCH_2)_2NCH_2CH_2OH$

Upon solidification, this product, a cream-colored hand wax, exhibited a melting point range of 42–45° C.

EXAMPLE 8

A two liter four neck round bottom flask equipped with a stirrer, thermometer, reflux condenser, and nitrogen inlet tube was charged with 625 g of 1,2-epoxyoctadecane, 2.14 moles based on an oxirane oxygen content of 5.48% and 161 g of N-methyl ethanolamine, 2.14 moles. With mild nitrogen purging, the mixture was stirred and heated to 100° C. A rapid exotherm set in, causing the temperature to rise to 160° C. Stirring was continued without external heating until the temperature fell to 80° C. The molten mass was cast into an aluminum pan, when it solidified at room temperature to a soft white wax, melting point range 30–55° C. The product had the following analytical values:

| | |
|---|---|
| Base Value | 150.79 mg |
| Hydroxyl Value | 305.85 mg |
| Primary Amine | 0.00 meq./gm. |
| Secondary Amine | 0.05 meq./gm. |
| Tertiary Amine | 2.64 meq./gm. |

These data show the product obtained to be the compound of the formula:

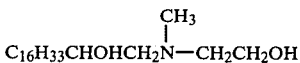

$$C_{16}H_{33}CHOHCH_2N\overset{\underset{\displaystyle CH_3}{|}}{\phantom{N}}-CH_2CH_2OH$$

EXAMPLE 9

A one liter four neck round bottom flask equipped with a stirrer, thermometer, reflux condenser, and nitrogen inlet tube was charged with 288 g of 1,2-epoxyoctadecane, 1.0 mole based on an oxirane oxygen content of 5.55% and 37.5 g of monoisopropanolamine, 0.5 mole. With mild nitrogen purging, the mixture was stirred and heated to 120° C. A rapid exotherm set in, causing the temperature to rise to 160° C. The temperature was raised to 170° C. causing an exotherm to 177° C. Stirring was continued without external heating until the temperature fell to 80° C. The molten mass was cast into an aluminum pan. The product had the following analytical values:

| | |
|---|---|
| Base Value | 84.28 mg |
| Hydroxyl Value | 249.69 mg. |
| Primary Amine | 0.07 meq./gm. |
| Secondary Amine | 0.11 meq./gm. |
| Tertiary Amine | 1.32 meq./gm. |

These data show the product obtained to be the compound of the formula:

$$(C_{16}H_{33}CHOHCH_2)_2NCH_2CHOHCH_3$$

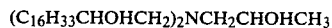

Upon solidification, this product, a white crystalline wax, exhibited a melting point range of 38–41° C.

EXAMPLE 10

A one liter four neck round bottom flask equipped with a stirrer, thermometer, reflux condenser, and nitrogen inlet tube was charged with 1, 2-epoxyoctadecane, 513 g, 1.78 mole, based on an oxirane oxygen content of 5.55% of 2amino and- 2ethyl-1, 3-propanediol, 106 g, 0.089 mole. With mild nitrogen purging, the mixture was stirred and heated to 120° C., A mild exotherm set in, causing the temperature to rise to 152° C. Stirring was continued without external heating until the temperature fell to 80° C. The molten mass was cast into an aluminum pan. The product had the following analytical values:

| | |
|---|---|
| Base Value | 79.01 mg |
| Hydroxyl Value | 313.17 mg |
| Primary Amine | 0.0 meq./gm. |
| Secondary Amine | 0.0 meq./gm. |
| Tertiary Amine | 1.42 meq./gm. |

These data show the product obtained to be the compound of the formula:

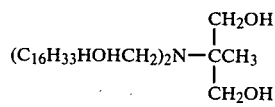

$$(C_{16}H_{33}HOHCH_2)_2N-\overset{\underset{\displaystyle CH_2OH}{|}}{\underset{|}{C}}CH_3$$
$$\phantom{(C_{16}H_{33}HOHCH_2)_2N-C}CH_2OH$$

Upon solidification, this product, a white, soft, crystalline wax, exhibited a melting point range of 35–39° C.

Further illustrations showing the use of the compounds discussed hereinabove in personal care compositions are set forth in the following examples.

EAMPLE 11

Hand Lotion

| | % |
|---|---|
| Tertiary amine of Example 2 | 1.0 |
| Polychol 20 (Croda) | 1.8 |
| [polyoxyethylene (20) - lanolin ether] | |
| Carsemul SC 73 | 2.9 |
| [cetyl and stearyl alcohol and their 20 mole ethoxylates] | |
| Pegosperse 50 MS (Glyco) | 0.8 |
| [glycol stearate] | |
| G.E. Silicone Fluid SF 96 (100) | 4.0 |
| [dimethicone] | |
| Mineral Oil | 4.5 |
| Lactic Acid | 0.25 |
| Preservatives, perfume and | |
| Deionized Water q.s. | 100 |

EXAMPLE 12

Hair Conditioner and Creme Rinse

| | % |
|---|---|
| Tertiary amine from Example 2 | 2.0 |
| Cetyl Alcohol | 2.3 |
| Aldo MSA (Glyco) | 6.0 |
| [glycerol Monostearate (Acid Stable)] | |
| Volpo 5 | 2.9 |
| [Polyoxyethylene (5) olyl ether] | |
| Stearyl Alcohol | 1.5 |
| Crodamol DA (Croda) | 1.0 |
| [di-isopropyl adipate] | |
| Carsamide AMEA-70 | 7.5 |
| [2-hydryethylacidamide] | |
| Carsemol N-520 | 0.5 |
| [C$_{12-15}$ alkyl polyoxyethylene (12)-oleate] | |
| G.E. Silicone Fluid SF-96 (100 csk) | 1.4 |
| [dimethicone] | |
| Carsoquate SDQ-85 | 0.2 |
| [Stearalkonium chloride] | |
| Lactic Acid (88%) | 0.5 |
| Preservatives, perfume and | |
| Deionized water q.s. | 100 |

The lactic acid salt of the product shown in Example 2 when emulsified with cetyl alcohol shows excellent conditioning properties. This conditioner was applied to Negroid, Caucasoid, and Oriental hair. A softer feel of the hair was noticed with the general comment that the hair felt better. Fluffiness of the hair rather than limpness after application seemed to be another benefit of this amine salt.

Generally, personal care compositions for hair or skin include 1-5 weight percent of the salt of the tertiary amines discussed above, 1-10 weight percent of a fatty alcohol containing from 14 to 20 carbon atoms dispersed in water. Examples of such fatty alcohols include cetyl and stearyl alcohol. In addition, up to 2% of a thickener such as sodium chloride or a cellulose gum can be used as well as the other additives are illustrated in Examples 11 and 12. It should be understood, that yet other additives are also within the scope of the invention.

The preceding examples, as is apparent to those skilled in the art, can be modified. This invention, therefore, is not to be limited to the specific examples employed, and various changes can be made without departing from the spirit or the scope thereof.

What is claimed is:

1. A water base skin and hair care composition including:
   (a) 1-10 weight % of a fatty alcohol having from 14 to 20 carbon atoms;
   (b) 1-5 weight % of a salt of a tertiary amine, the amine selected from the group consisting of:

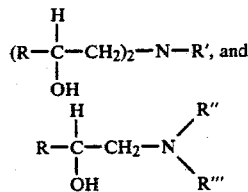

and mixture thereof, wherein
   R is a linear $C_8$ to $C_{20}$ alkyl group,
   R' is a hydroxyalkyl or polyhyroxyalkyl group having from 1 to 20 carbon atoms and one to five hydroxy groups per R',
   R" and R'" are, individually, linear alkyl, hydroxyalkyl or polyhydroxyalkyl groups, each having from 1 to 6 carbon atoms and 1 to 5 hydroxyl groups per R" or R'" and wherein said salt is nontoxic to the skin or scalp;
   (c) 0-2% of a thickener for composition; and
   (d) the remainder being water.

2. The composition according to claim 1 wherein the tertiary amine is:

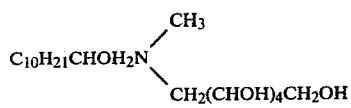

3. The composition according to claim 1 wherein the tertiary amine is:

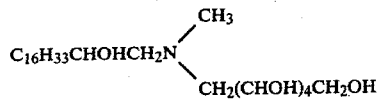

4. The composition according to claim 2, or 3, wherein the tertiary amine salt is selected from the group consisting of hydrochloric acid, citric acid, phosphoric acid and lactic acid salts.

5. The composition according to claim 1 wherein the tertiary amine is:

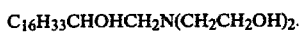

6. The composition according to claim 1 wherein the tertiary amine is:

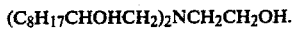

7. The composition according to claim 1 wherein the tertiary amine is:

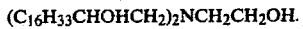

8. The composition according to claim 1 wherein the tertiary amine is:

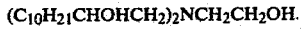

9. The composition according to claim 1 wherein the tertiary amine is:

* * * * *